(12) United States Patent
Yan et al.

(10) Patent No.: US 10,948,430 B2
(45) Date of Patent: Mar. 16, 2021

(54) METHOD AND DEVICE FOR DETERMINING CT SYSTEM PARAMETER

(71) Applicant: Shenzhen Our New Medical Technologies Development Co., Ltd., Shenzhen (CN)

(72) Inventors: Hao Yan, Shenzhen (CN); Wen Wang, Shenzhen (CN); Jinsheng Li, Shenzhen (CN)

(73) Assignee: SHENZHEN OUR NEW MEDICAL TECHNOLOGIES DEV CO., LTD

( * ) Notice: Subject to any disclaimer, the term of this patent is extended or adjusted under 35 U.S.C. 154(b) by 0 days.

(21) Appl. No.: 16/627,255

(22) PCT Filed: Jun. 27, 2017

(86) PCT No.: PCT/CN2017/090378
§ 371 (c)(1),
(2) Date: Dec. 27, 2019

(87) PCT Pub. No.: WO2019/000234
PCT Pub. Date: Jan. 3, 2019

(65) Prior Publication Data
US 2020/0132612 A1    Apr. 30, 2020

(51) Int. Cl.
*G01N 23/046* (2018.01)
(52) U.S. Cl.
CPC ..... *G01N 23/046* (2013.01); *G01N 2223/303* (2013.01); *G01N 2223/306* (2013.01)
(58) Field of Classification Search
CPC ........... G01N 23/046; G01N 2223/303; G01N 2223/306; A61B 6/03; G01B 11/03
See application file for complete search history.

(56) References Cited

U.S. PATENT DOCUMENTS 4,922,915 A * 5/1990 Arnold .................. A61B 6/583
378/18
5,699,446 A * 12/1997 Rougee ................... A61B 6/02
382/130
(Continued)

FOREIGN PATENT DOCUMENTS

CN    101750021 A    6/2010
CN    102652674 A    9/2012
(Continued)

OTHER PUBLICATIONS

International Search Report in International Patent Application No. PCT/CN2017/090378 dated Mar. 26, 2018, in 4 pages.

*Primary Examiner* — Marcus H Taningco
(74) *Attorney, Agent, or Firm* — Knobbe Martens Olson & Bear LLP

(57) ABSTRACT

A method for determining a CT system parameter: controlling a mould body to move between an X-ray source and a detection surface of a detector, and acquiring X-ray projections of the mould body during movement on the detection surface, wherein the mould body has a first plane and a second plane perpendicular to each other, and the first plane and the second plane are always perpendicular to the detection surface during the movement of the mould body; determining a first straight line and a second straight line according to the acquired X-ray projections; and determining an intersection point of the first straight line and the second straight line as a pedal coordinate of a focus of the X-ray source on the detection surface, a CT coordinate system parameter including the coordinates of the foot of the perpendicular.

19 Claims, 11 Drawing Sheets

(56) References Cited

U.S. PATENT DOCUMENTS

| | | | |
|---|---|---|---|
| 5,872,829 A | 2/1999 | Wischmann et al. | |
| 7,170,966 B2 | 1/2007 | Kuo-Petravic et al. | |
| 7,582,860 B2 * | 9/2009 | Kusunoki | A61B 6/583 |
| | | | 250/252.1 |
| 2013/0114799 A1 * | 5/2013 | Yamakawa | A61B 6/14 |
| | | | 378/207 |
| 2015/0305696 A1 * | 10/2015 | Yamakawa | A61B 6/14 |
| | | | 378/19 |
| 2018/0120243 A1 * | 5/2018 | Yashima | G01B 15/045 |

FOREIGN PATENT DOCUMENTS

| | | |
|---|---|---|
| CN | 105931202 A | 9/2016 |
| CN | 106706675 A | 5/2017 |

* cited by examiner

03

METHOD AND DEVICE FOR DETERMINING CT SYSTEM PARAMETER

CROSS-REFERENCE TO RELATED APPLICATION

This application is a 371 of PCT international patent application No.: PCT/CN2017/090378 filed on Jun. 27, 2017.

TECHNICAL FIELD

The present disclosure relates to the field of computer imaging technology, and more particularly to method and device for determining CT system parameter.

BACKGROUND

A computed tomography (CT) system is a computer imaging system capable of acquiring images of the interior of an object in a non-destructive manner. The CT system includes: an X-ray (also known as Roentgen ray) source and a detector. The CT system needs to use a CT system parameter (such as coordinates of a foot of a perpendicular of a focus of the X-ray source on a detection surface of the detector) in the process of acquiring images. Therefore, the CT system parameter needs to be determined before using the CT system to acquire the images.

In the process of determining the parameters of a traditional CT system, a fine-structure customized mould body is required. The mould body is a structural part embedded with a plurality of small steel balls. Specifically, the customized mould body may be placed between the X-ray source and the detection surface of the detector, and the X-ray source is controlled to emit X-rays to the detection surface. Then, X-ray projections of the plurality of small steel balls on the detection surface are acquired. Further, the acquired X-ray projections are analyzed to determine the coordinates of the foot of the perpendicular of the focus of the X-ray source on the detection surface of the detector in geometric parameters of the CT system.

In the related art, the customized mould body is required to determine the CT system parameter. However, a manufacturing process of the mould body is relatively complicated because of a higher machining accuracy requirement on the structure of the customized mould body.

SUMMARY

In order to solve the problem of the relatively complicated manufacturing process of the mould body, the present disclosure provides a method and a device for determining a CT system parameter. The technical solutions are as follows.

In a first aspect, there is provided a method for determining a computed tomography (CT) system parameter. A CT system includes: an X-ray source and a detector. The method includes: controlling a mould body to move between the X-ray source and a detection surface of the detector, and acquiring X-ray projections of the mould body during movement on the detection surface, wherein the mould body has a first plane and a second plane perpendicular to each other and the first plane and the second plane are always perpendicular to the detection surface during the movement of the mould body; determining a first straight line and a second straight line according to the acquired X-ray projections, wherein the first straight line is a straight line of a projection line segment of an edge of the first plane in boundary line segments of the acquired X-ray projections, the second straight line is a straight line of a projection line segment of an edge of the second plane in the boundary line segments of the acquired X-ray projections, a plane determined by the first straight line and a focus of the X-ray source is perpendicular to the detection surface, and a plane determined by the second straight line and the focus of the X-ray source is perpendicular to the detection surface; and determining an intersection point of the first straight line and the second straight line as coordinates of a foot of a perpendicular of the focus of the X-ray source on the detection surface, wherein a CT coordinate system parameter includes the coordinates of the foot of the perpendicular.

In a second aspect, there is provided a device for determining a CT system parameter, including at least one processor, at least one interface, a memory and at least one communication bus, wherein the processor is configured to execute a program stored in the memory to implement the method for determining CT system parameter in the first aspect.

In a third aspect, there is provided a computer-readable storage medium. Instructions are stored in the computer-readable storage medium. When the computer-readable storage medium runs on a computer, the computer is caused to execute the method for determining a CT system parameter in the first aspect.

In a fourth aspect, there is provided a computer program product including instructions. When the computer program product runs on a computer, the computer is made to execute the method for determining a CT system parameter in the first aspect.

The technical solutions provided by the present disclosure have the following beneficial effects. The CT system parameter can be determined as long as the used mould body has the first plane and the second plane. Moreover, since the structure of the plane is relatively simple, a manufacturing process of the mould body is relatively simple. Optionally, the mould body used in the present disclosure may be a scanning table or a light-limiting door in the CT system. That is, an intrinsic component in the CT system is directly used as the mould body in the present disclosure and thus there is no need to use a customized module body in the process of determining the CT system parameter.

BRIEF DESCRIPTION OF THE DRAWINGS

In order to describe the technical solutions in the embodiments of the present disclosure more clearly, the following briefly introduces the accompanying drawings required for describing the embodiments. Apparently, the accompanying drawings in the following description show merely some embodiments of the present disclosure, and a person of ordinary skill in the art may also derive other drawings from these accompanying drawings without creative efforts.

DETAILED DESCRIPTION

In order to make the objects, technical solutions and advantages of the present disclosure clearer, embodiments of the present disclosure will be further described in detail below with reference to the accompanying drawings.

Figure 1:
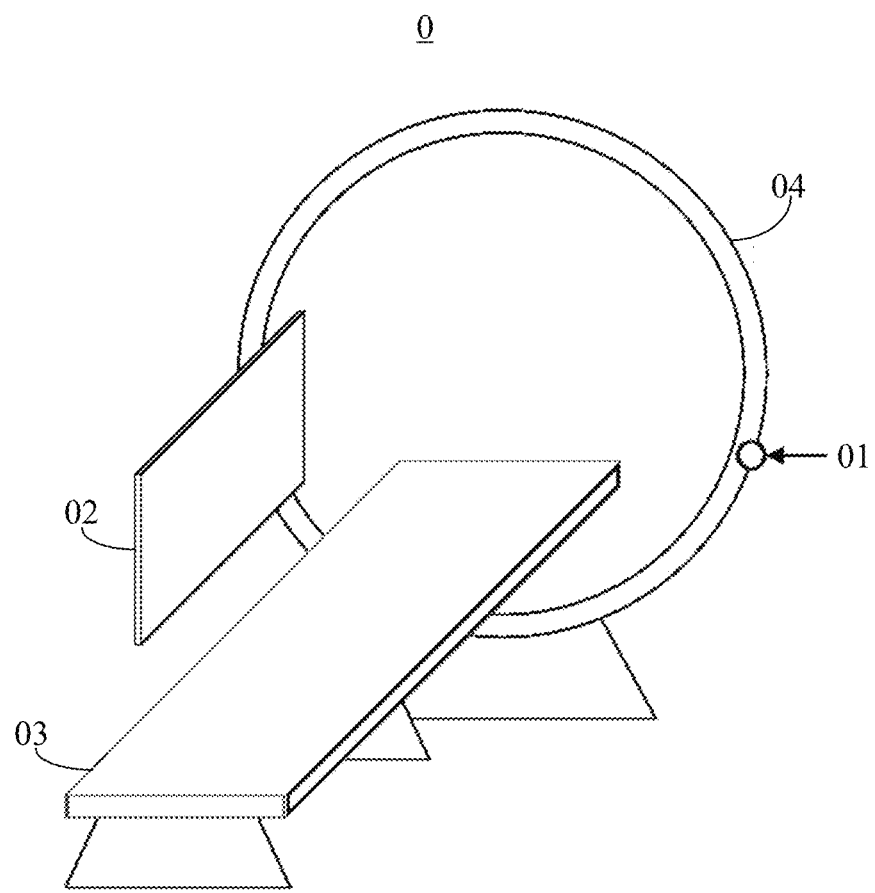
FIG. 1 is a schematic view showing a structure of a CT system provided by an embodiment of the present disclosure.

FIG. 1 is a schematic view showing a structure of a CT system provided by an embodiment of the present disclosure. As shown in FIG. 1, the CT system 0 may include: an X-ray source 01, a detector 02, a scanning table 03, a light-limiting door (not shown in FIG. 1) of the X-ray source 01, a roller 04, and a control component (not shown in FIG. 1). The CT system may also be referred to as a cone-beam CT system, and a CT system parameter may also be referred to as a geometric parameter of the CT system.

Optionally, both the X-ray source 01 and the detector 02 may be fixedly arranged on the roller 04, and the roller 04 can drive the X-ray source 01 and the detector 02 to rotate. The X-ray source 01 may also be referred to as a bulb tube. The detector 02 has a detection surface located at a light emission side of the X-ray source 01. The scanning table 03 is arranged between the detection surface and the X-ray source 01. The control component can control the scanning table 03 to move upwards or downwards, leftwards or rightwards, or backwards or forwards. The light-limiting door is arranged at a light emission portion of the X-ray source 01, and can limit light emitted from the X-ray source 01 to a preset range. Optionally, the control component can also control the light-limiting door to move.

Optionally, the CT system may further include a device for determining a CT system parameter (not shown in FIG. 1) in the following embodiments. The device for determining a CT system parameter may be a computer or other components having a processing function.

Figure 2:
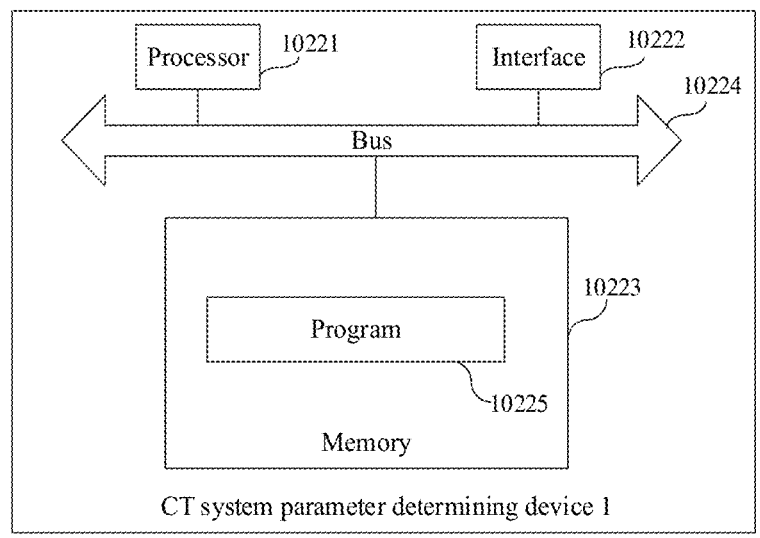
FIG. 2 is a schematic view showing a structure of a device for determining a CT system parameter provided by an embodiment of the present disclosure.

FIG. 2 is a schematic view showing a structure of a device for determining a CT system parameter 1 provided by an embodiment of the present disclosure. As shown in FIG. 2, the device for determining a CT system parameter 1 may include: at least one processor 10221 (for example, a central processing unit), at least one interface 10222, a memory 10223, and at least one bus 10224. The bus 10224 can be configured to implement connection and communication among the processor, the interface and the memory. The memory 10223 and the interface 10222 are respectively connected to the processor 10221 through the bus 10224. The processor 10221 is configured to execute an executable module, such as a computer program, stored in the memory 10223. The memory 10223 may include a high-speed random access memory (RAM), and may also include a non-volatile memory, such as at least one magnet disk memory. The communication connection between the device for determining a CT system parameter 1 and at least one other device is implemented through the at least one interface 10222 (in a wired or wireless manner). In some embodiments, the memory 10223 stores a program 10225 that can be executed by the processor 10221.

Figure 3:
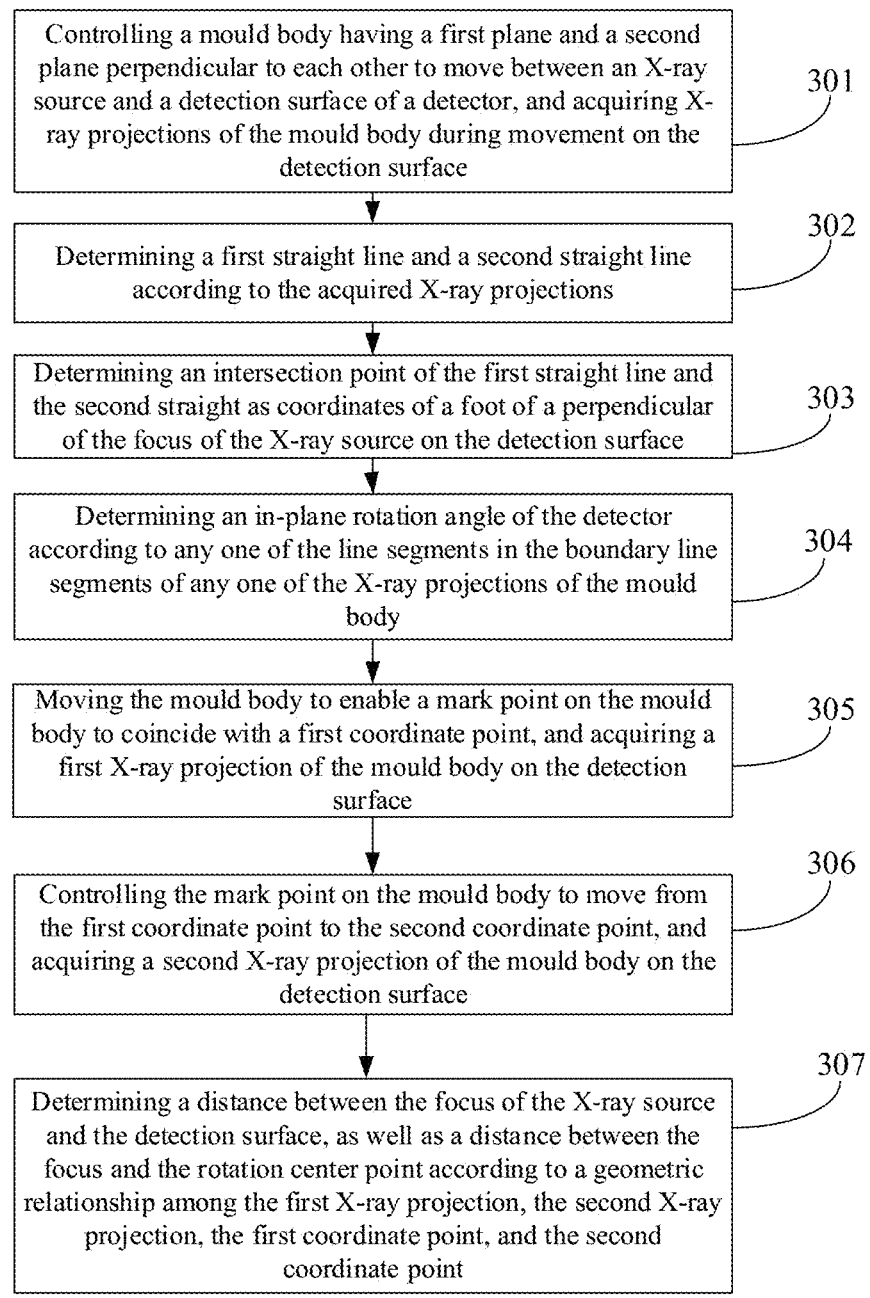
FIG. 3 is a flow chart of a method for determining a CT system parameter provided by an embodiment of the present disclosure.

FIG. 3 is a flow chart of a method for determining a CT system parameter provided by an embodiment of the present disclosure. The method for determining a CT system parameter may be configured to determine the CT system parameter as shown in FIG. 1, and may be used in the CT system parameter determining device as shown in FIG. 2. As shown in FIG. 3, the method for determining a CT system parameter may include the following steps.

In step 301, a mould body having a first plane and a second plane perpendicular to each other is controlled to move between an X-ray source and a detection surface of a detector, and X-ray projections of the mould body during movement on the detection surface are acquired.

Exemplarily, in the embodiment of the present disclosure, a mould body is required to be used in determination of the CT system parameter and the mould body is required to have a first plane and a second plane perpendicular to each other. That is, the mould body used in the embodiment of the present disclosure is a three-dimensional geometric structure having the first plane and the second plane.

Figure 4:
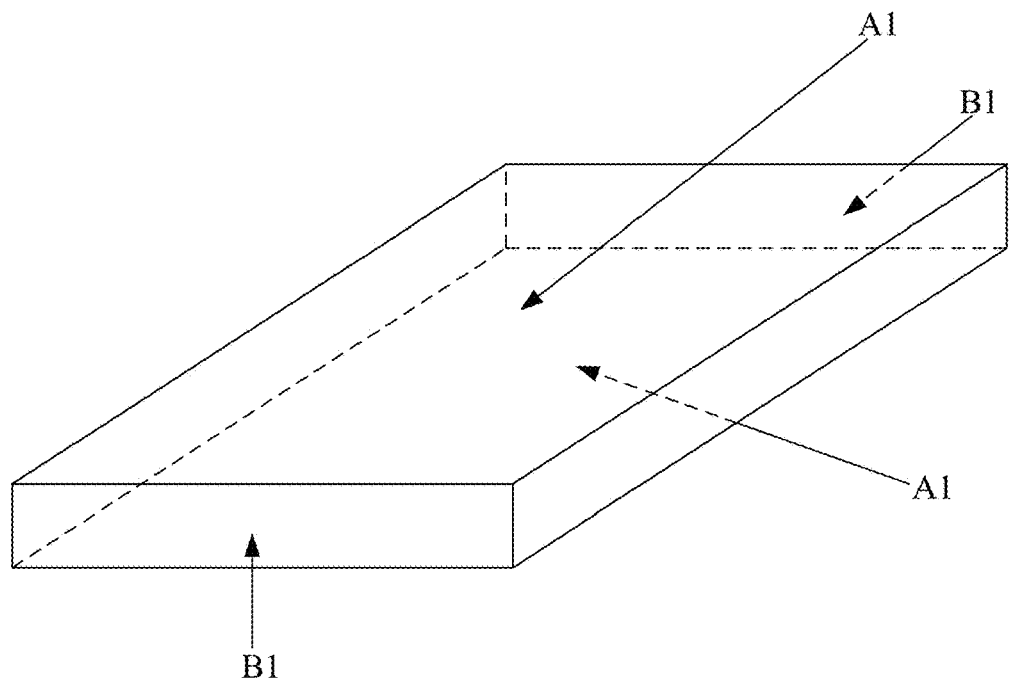
FIG. 4 is a schematic view showing a structure of a scanning table provided by an embodiment of the present disclosure.
Figure 5:
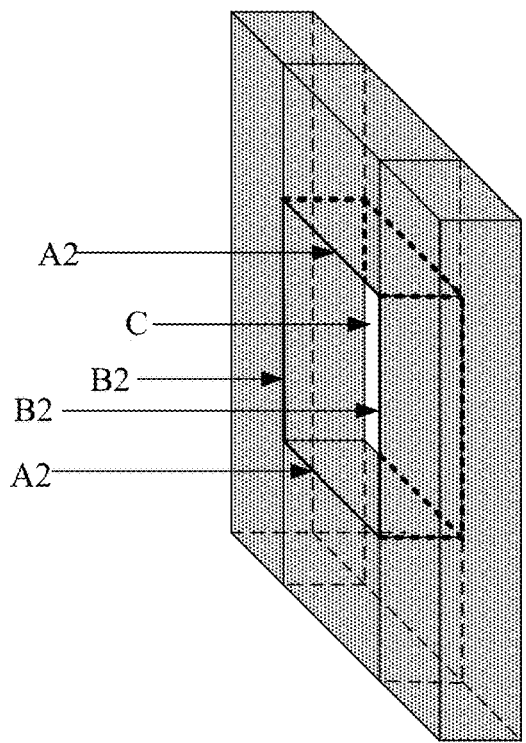
FIG. 5 is a schematic view showing a structure of a light-limiting door provided by an embodiment of the present disclosure.

FIG. 4 is a schematic view showing a structure of a scanning table 03 provided by an embodiment of the present disclosure. As shown in FIG. 4, the scanning table 03 may include a cubic structure, and has two first planes A1 and two second planes B1, and the first planes A1 are perpendicular to the second planes B1. That is, the scanning table in the CT system meets the requirement for the shape of the mould body in the embodiment of the present disclosure. Thus, the scanning table can be used as the mould body. FIG. 5 is a schematic view showing a structure of a light-limiting door provided by an embodiment of the present disclosure. As shown in FIG. 5, the light-receiving door is of a structure with a rectangular through-hole C formed in the middle thereof. Four surfaces, which are around and form the rectangular through-hole C, include two first planes A2 and two second planes B2, and the first planes A1 are perpendicular to the second planes B1. That is, the light-limiting door in the CT system also meats the requirement for the shape of the mould body in the embodiment of the present disclosure. Thus, the light-limiting door can also be used as the mould body.

It should be noted that in the embodiment of the present disclosure, the scanning table or the light-limiting door in the CT system is used as the mould body is taken as an example. In a practical application, the mould body may also be other geometric structure having the first plane and the second plane, which is not limited in the embodiments of the present disclosure.

Figure 6:
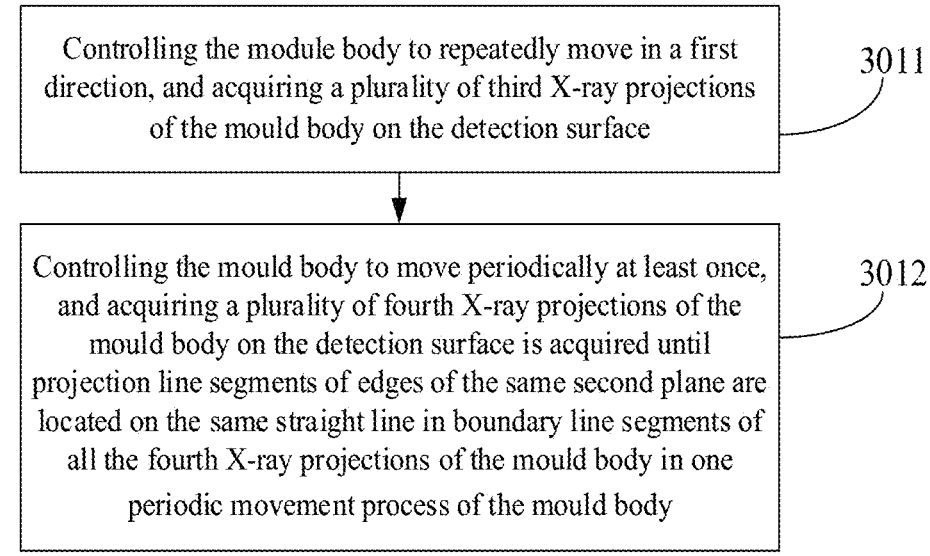
FIG. 6 is a flow chart of a method for acquiring X-ray projections provided by an embodiment of the present disclosure.

FIG. 6 is a flow chart of a method for acquiring X-ray projections provided by an embodiment of the present disclosure. As shown in FIG. 6, the step 301 may include the following sub-steps.

In step 3011, the module body is controlled to move multiple times in a first direction, and a plurality of third X-ray projections of the mould body on the detection surface is acquired.

Figure 7:
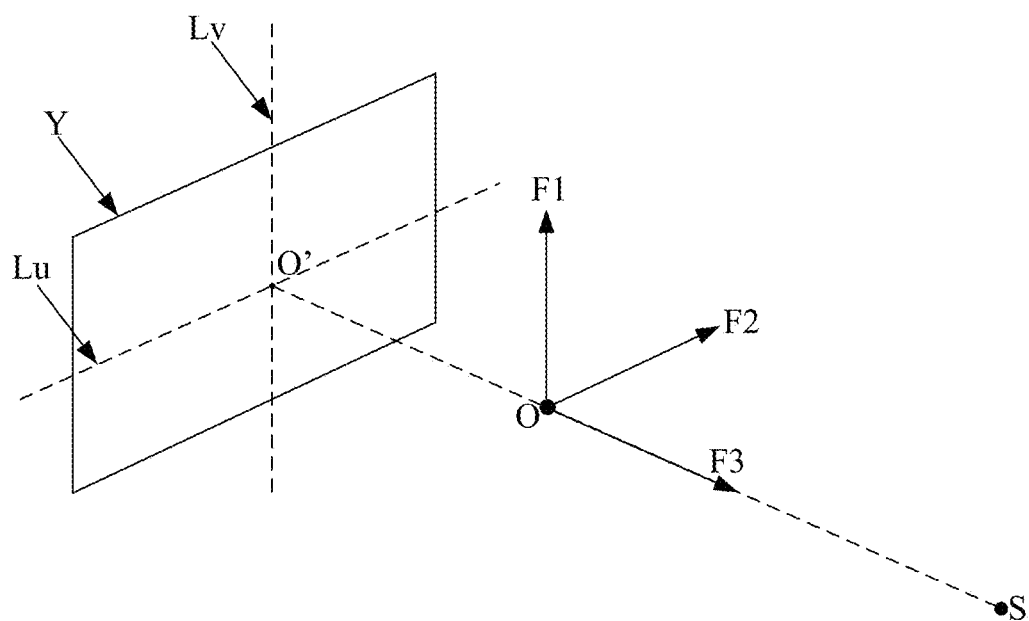
FIG. 7 is a schematic view showing a direction and position of the CT system provided by an embodiment of the present disclosure.

It should be noted that, when acquiring the X-ray projections by the method shown in FIG. 6, the mould body needs to have m first planes which are parallel to each other, and m is an integer greater than or equal to 2. FIG. 7 is a schematic view showing a direction and position of the CT system provided by an embodiment of the present disclosure. As shown in FIG. 7, a first direction F1 may be perpendicular to a first plane (and parallel to a detection surface Y). In step 3011, the mould body may be controlled to move multiple times in the first direction F1, after each time the mould body moves in the first direction F1, the X-ray source is controlled to emit X-rays to the detection surface of the detector to make an exposure to the mould body and acquire the third X-ray projection of the mould body on the detection surface Y.

Exemplarily, the mould body may be moved to a top end (i.e., moved to a maximum value of a top in a range of up and down movement of the mould body) or a bottom end (i.e., moved to a maximum value of a bottom in a range of up and down movement of the mould body). Then, the mould body is moved slowly at a constant speed in the first direction or a direction opposite to the first direction (the distance of each movement may be the same, and may be as small as possible). In this process, the mould body may be continuously exposed. Optionally, referring to FIG. 7, a rotation center point O of the CT system may be located between a focus S of the X-ray source and the detection surface Y. A line of the rotation center point O and the focus S is perpendicular to the detection surface Y. In step 3011, first, the mould body may be moved to the rotation center point O, and then the mould body is moved multiple times from the rotation center point O in the first direction F1. Exemplarily, when controlling the movement of the mould body, a mould body control component can control the mould body to move upwards or downwards, leftwards or rightwards, or backwards or forwards. When the mould body is a scanning table, the mould body control component may include: an upper computer and a lower computer in the CT system.

Figure 8:
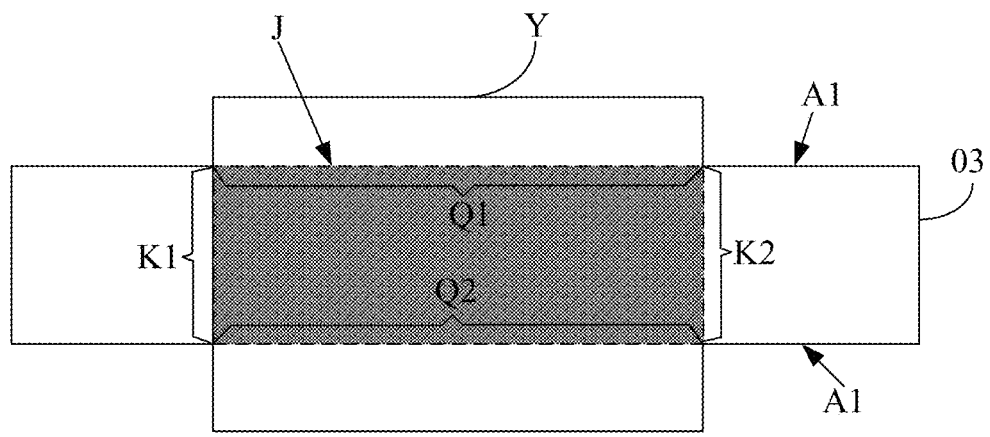
FIG. 8 is a schematic diagram of a third X-ray projection provided by an embodiment of the present disclosure.

FIG. 8 is a schematic diagram of a third X-ray projection provided by an embodiment of the present disclosure. As shown in FIG. 8, the scanning table 03 is taken as the mould body and the third X-ray projection of the mould body on the detection surface Y is a rectangle J. A boundary line segment of the third X-ray projection (namely, a boundary line segment of the rectangle J) may include: a line segment Q1, a line segment Q2, a line segment K1, and a line segment K2. The line segment Q1 and the line segment Q2 are projection line segments of edges of the two first planes A1 of the mould body on the detection surface Y, respectively.

After each time the mould body is moved in step 3011, the boundary line segment of the third X-ray projection of the mould body on the detection surface Y needs to include: projection line segments of the edges of the two first planes in the m first planes. After multiple times of movements of the mould body, the projection line segments of the edges of two same first planes in the boundary line segments of each third X-ray projection can be acquired, so that a plurality of sets of parallel projection line segments can be acquired.

In step 3012, the mould body is controlled to perform at least one periodic movement and acquire a plurality of fourth X-ray projections of the mould body on the detection surface, until in one periodic movement process of the mould body, projection line segments of edges of the same second plane in boundary line segments of all the fourth X-ray projections of the mould body are located on the same straight line.

Exemplarily, a second direction may be perpendicular to the second plane. A third direction is perpendicular to both the first direction and the second direction. The one periodic movement performed by the mould body may include: controlling the mould body to move in the second direction, and controlling the mould body to move multiple times in the third direction after the mould body is controlled to move in the second direction. The fourth X-ray projection is the X-ray projection of the mould body on the detection surface during the movement in the third direction. Please continue to refer to FIG. 7, a second direction F2 is parallel to the detection surface Y, and a third direction F3 is perpendicular to both the first direction F1 and the second direction F2. In step 3012, the mould body can be controlled to perform at least one periodic movement at any one coordinate point. That is, the mould body is controlled to move in the second direction F2 at least once, and is controlled to move multiple times in the third direction F3 after each time the mould body is controlled to move in the second direction.

It should be noted that after each time the mould body is controlled to move in the third direction F3, it is required to control the X-ray source to emit X-rays to the detection surface of the detector to expose the mould body once, and acquire a fourth X-ray projection of the mould body on the detection surface. It should be noted that when the mould body is the scanning table, the boundary line segment of the fourth X-ray projection of the mould body on the detection surface may not include the projection line segment of the edge of the second plane. Thus, it is required to continuously move the mould body in the second direction to make the boundary line segment of the fourth X-ray projection of the mould body on the detection surface include the projection line segment of the edge of the second plane, until in one periodic movement process of the mould body, the projection line segments of edges of the same second plane in the boundary line segments of all the fourth X-ray projections are located on the same straight line.

Figure 9:
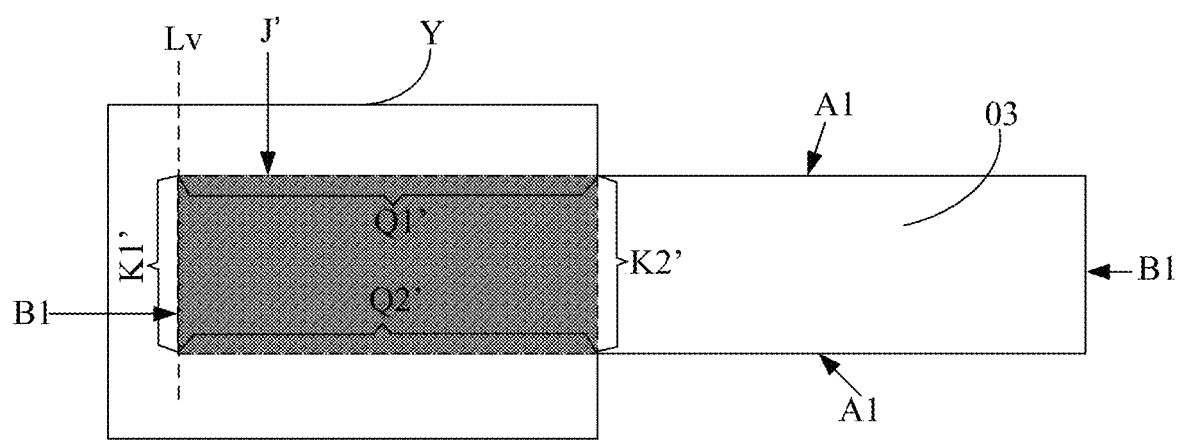
FIG. 9 is a schematic diagram of a fourth X-ray projection provided by an embodiment of the present disclosure.

FIG. 9 is a schematic diagram of a fourth X-ray projection provided by an embodiment of the present disclosure. FIG. 9 uses that the mould body is the scanning table 03 as an example, and the view shown in FIG. 9 is a view directly facing the detection surface. When the mould body is controlled to stop moving in the second direction, the fourth X-ray projection of the mould body on the detection surface Y is a rectangle J', and a boundary line segment of the fourth X-ray projection (i.e., a boundary line segment of the rectangle J') may include: a line segment Q1', a line segment Q2', a line segment K1', and a line segment K2'. The line segment Q1' and the line segment Q2' are projection line segments of the edges of the two first planes A1 of the mould body on the detection surface Y, respectively. The line segment K1' is a projection line segment of an edge of one second plane B1 of the mould body on the detection surface Y. The boundary line segments of the fourth X-ray projections of the mould body on the detection surface include: the projection line segments of the edges of the two first planes on the detection surface, and the projection line segment of the edge of the second plane on the detection surface.

If projection line segments (e.g., one of the projection line segments is the line segment K1') of the edge of one second plane of the mould body in the boundary line segment of all the fourth X-ray projections in one periodic movement of the mould body are located on the same straight line Lv, the mould body may be controlled to stop moving.

In step 302, a first straight line and a second straight line are determined according to the acquired X-ray projections.

Figure 10:
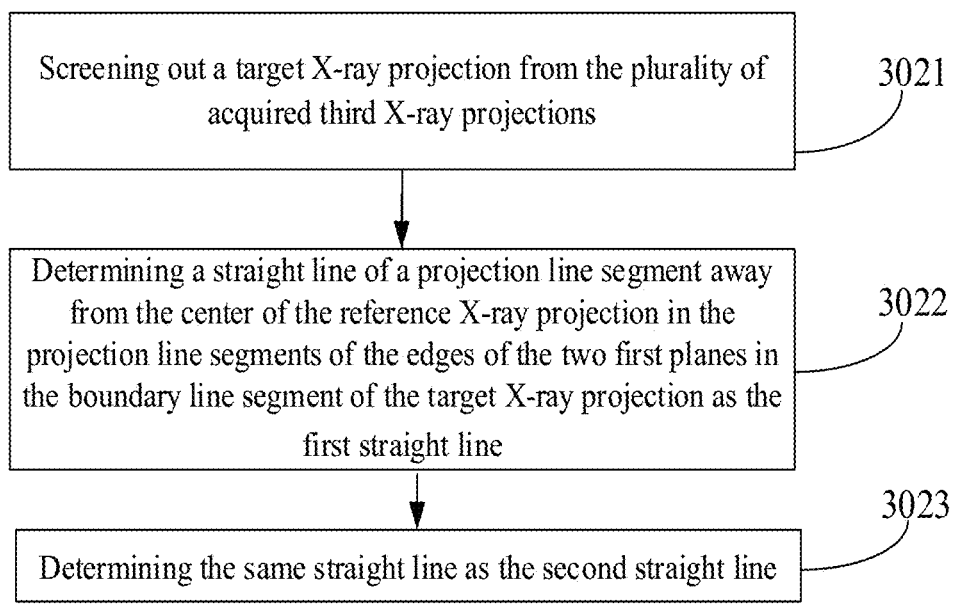
FIG. 10 is a flow chart of a method for determining a first straight line and a second straight line provided by an embodiment of the present disclosure.

As shown in FIG. 10, step 302 may include the following sub-steps.

In step 3021, a target X-ray projection is screened out from the plurality of acquired third X-ray projections.

The target X-ray projection is a projection with the minimum distance between the projection line segments of the edges of the two first planes (the first plane Z1 and the first plane Z2) among the boundary line segments of the plurality of third X-ray projections. A reference X-ray projection and the target X-ray projection are two X-ray projections continuously acquired from the plurality of third X-ray projections. A distance between the projection line segments of the edges of the two first planes (the first plane Z1 and the first plane Z2) in the boundary line segments of the target X-ray projection is less than a distance between the projection line segments of the edges of the two first planes (the first plane Z1 and the first plane Z2) in the boundary line segments of the reference X-ray projection.

Figure 11:
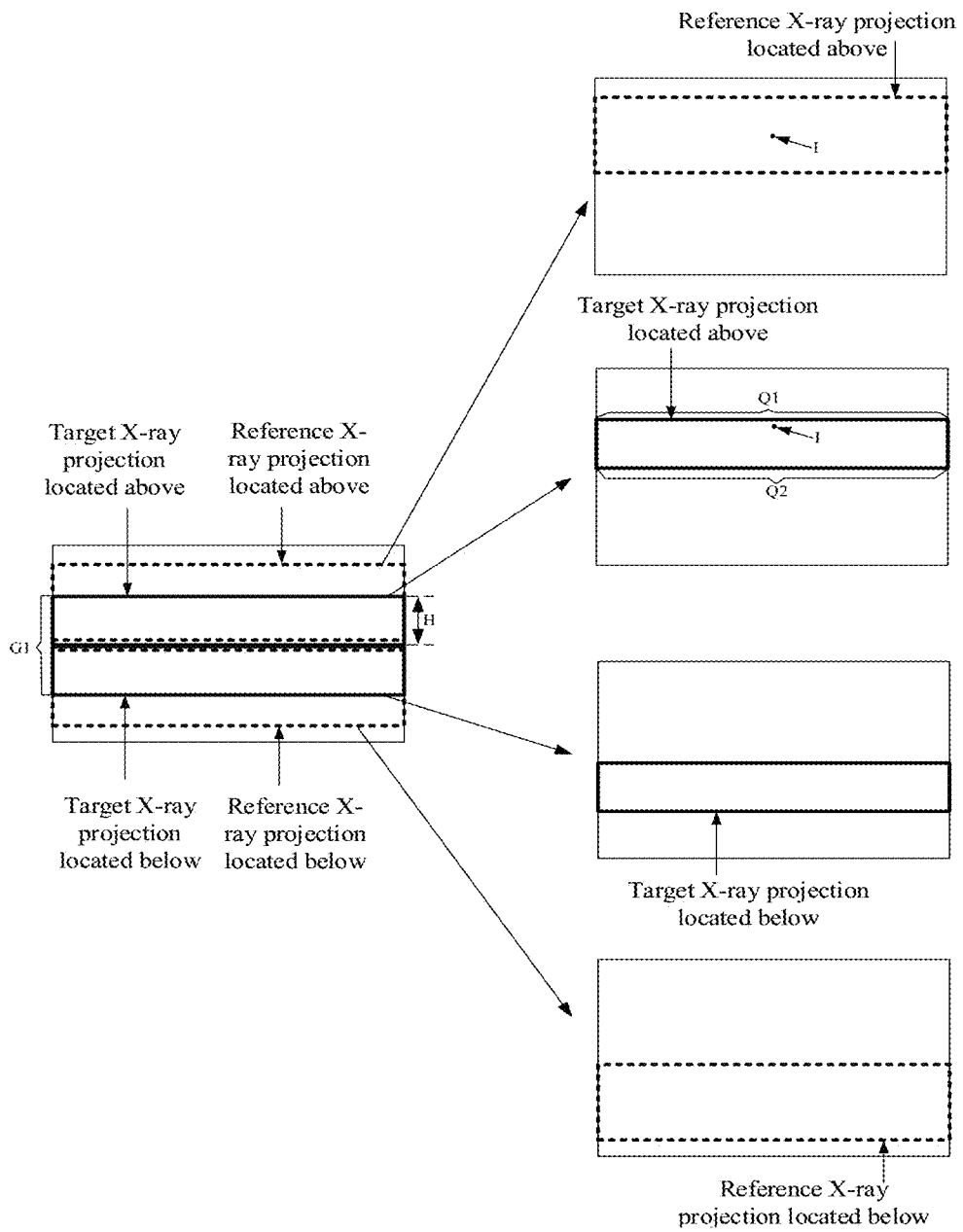
FIG. 11 is a schematic diagram of a target X-ray projection provided by an embodiment of the present disclosure.

As shown in FIG. 11, in the mould body movement process, a plurality of third X-ray projections may be acquired, wherein distances H of two projection line segments of the edges of the two first planes are all equal in the boundary line segments of all the third X-ray projections located in a range G1; and the third X-ray projection in the range G1 is the third X-ray projection in which the distance between the projection line segments of the edges of the two first planes is the shortest in the boundary line segments of all the third X-ray projections.

The reference X-ray projection is a third X-ray projection adjacent to the range G1 in the plurality of third X-ray projections. Exemplarily, there are two reference X-ray projections in FIG. 11. After acquiring the reference X-ray projection located below, the mould body is controlled to move upwards to obtain a third X-ray projection (referred to as the target X-ray projection located below in the embodiment of the present disclosure) in the range G1. After acquiring the reference X-ray projection located above, the mould body is controlled to move downwards to obtain a third X-ray projection (referred to as the target X-ray projection located above in the embodiment of the present disclosure) in the range G1. That is, there are two target X-ray projections (the target X-ray projection located above and the target X-ray projection located below) in the range G1. In step 3021, either of the target X-ray projections may be selected. Optionally, in step 3021, the target X-ray projection located above may be selected as an example from the two target X-ray projections. In a practical application, the target X-ray projection located below can also be selected in step 3021.

In step 3022, a straight line of a projection line segment away from the center of the reference X-ray projection in the projection line segments of the edges of the two first planes in the boundary line segment of the target X-ray projection is determined as the first straight line.

Please continue to refer to FIG. 11, the boundary line segment of the target X-ray projection (the target X-ray projection located above) may include projection line segments Q1 and Q2 of the edges of the two first planes. In the projection line segments of the edges of the two first planes, there is a projection line segment Q1 close to a center I of the reference X-ray projection (as the target X-ray projection and the reference X-ray projection are two third X-ray projections continuously acquired, the reference X-ray projection is the reference X-ray projection located above), and there is a projection line segment Q2 away from the center I of the reference X-ray projection. In step 3022, a straight line of the projection line segment Q2 away from the reference X-ray projection may be determined as the first straight line. A plane determined by the first straight line and a focus of the X-ray source is perpendicular to the detection surface.

In step 3023, the same straight line is determined as the second straight line.

After determining that the projection line segments of the edges of the same second plane are all located on the same straight line in step 3012, it can be determined that the same straight line is the second straight line. A plane determined by the second straight line and the focus of the X-ray source is perpendicular to the detection surface.

In step 303, an intersection point of the first straight line and the second straight line is determined as coordinates of a foot of a perpendicular of the focus of the X-ray source on the detection surface.

Exemplarily, a CT system parameter may include the coordinates of the foot of the perpendicular of the focus of the X-ray source on the detection surface. Please continue to refer to FIG. 7, if the first straight line is Lu and the second straight line is Lv, in step 303, coordinates of the intersection point O' of the first straight line Lu and the second straight line Lv may be determined as the coordinates of the foot of the perpendicular of the focus S of the X-ray source on the detection surface Y.

In step 304, an in-plane rotation angle of the detector is determined according to any one of the line segments in the boundary line segments of any one of the X-ray projections of the mould body.

Optionally, a plurality of X-ray projections is acquired in step 301. In step 304, the in-plane rotation angle of the detector can be determined according to any one of the line segments in the boundary line segments of any one of the X-ray projections acquired in step 301.

Figure 12:
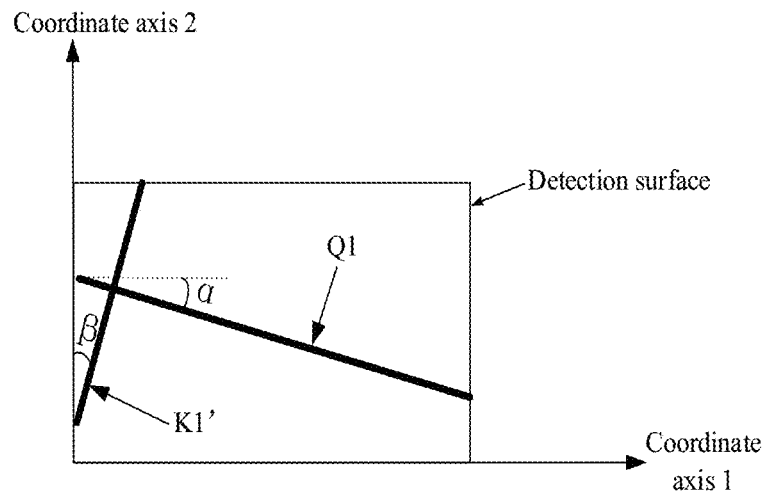
FIG. 12 is a schematic diagram of an in-plane rotation angle provided by an embodiment of the present disclosure.

Exemplarily, as shown in FIG. 12, a two-dimensional coordinate system may be established on the detection surface. The origin of the two-dimensional coordinate system may be an apex angle of the detection surface; and two coordinate axes (a coordinate axis 1 and a coordinate axis 2) of the two-dimensional coordinate system may be the two edges constituting the apex angle on the detection surface, respectively.

On one hand, if one of the planes is the first plane, and a projection line segment of an edge of the first plane is Q1, an angle α formed by the projection line segment Q1 and the longer edge of the detection surface (which is rectangular) can be calculated according to the location of Q1 in the two-dimensional coordinate system and a geometric relationship and α is used as the in-plane rotation angle of the detector.

On the other hand, if one of the planes is the second plane, and a projection line segment of an edge of the second plane is K1', an angle β formed by the projection line segment K1' and the shorter edge of the detection surface (which is rectangular) can be calculated according to the location of K1' in the two-dimensional coordinate system and the geometric relationship and β is used as the in-plane rotation angle of the detector.

In step 305, the mould body is moved to make a mark point on the mould body to coincide with a first coordinate point, and a first X-ray projection of the mould body on the detection surface is acquired.

The mould body may be provided with the mark point which may be located at any location on the mould body. Optionally, the mark point may be located on one of the first planes on the mould body. The first coordinate point may be located on a plane which passes through the rotation center point and parallel to the first plane. Optionally, the first coordinate point may coincide with the rotation center point. In step 305, the mould body may be controlled to move to make the mark point on the mould body to move to the first coordinate point; and the X-ray source is controlled to emit X-rays to the detection surface of the detector to make an exposure of the mould body, so as to acquire the first X-ray projection.

Figure 13:
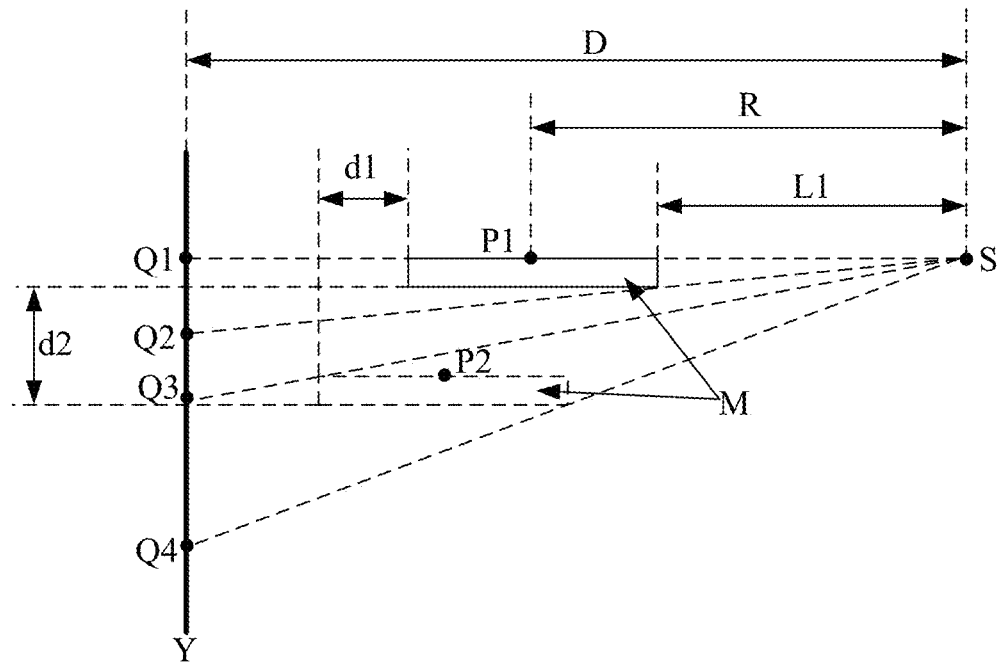
FIG. 13 is a schematic view showing a direction and position of another CT system provided by an embodiment of the present disclosure.

Exemplarily, FIG. 13 is a schematic view showing a direction and position of another CT system provided by an embodiment of the present disclosure. It should be noted that FIG. 13 is a front view of the CT system. As shown in FIG. 13, when the mark point coincides with the first coordinate point, both the first coordinate point and the mark point may be located at the location of a point P1 which may be located at the center of one of the first planes of the mould body M. Of course, the P1 is not necessarily located at the center of one of the first planes of the mould body M, which is not limited in the embodiments of the present disclosure.

In a first implementable manner, the boundary line segment of the first X-ray projection may at least include the projection line segments of the edges of the two first planes in the mould body M on the detection surface Y, which are a line segment Q1 and a line segment Q2 (since FIG. 13 is a side view of the detector, both the line segments Q1 and Q2 are represented as points). In a second implementable manner, the boundary line segment of the first X-ray projection may at least include a projection line segment (not shown in FIG. 13) of an edge of one second plane in the mould body M on the detection surface Y, and the length of the projection line segment is equal to the distance between Q1 and Q2 in FIG. 13.

In step 306, the mark point on the mould body is controlled to move from the first coordinate point to the second coordinate point, and a second X-ray projection on the mould body on the detection surface is acquired.

Please continue to refer to FIG. 13, in step 306, the mold body M may be controlled to move from the first coordinate point P1 to the second coordinate point P2; and the X-ray source is controlled to emit X-rays to the detection surface of the detector to make an exposure of the mould body, so as to acquire the second X-ray projection. Exemplarily, in FIG. 13, the mould body is moved by d1 from the first coordinate point P1 in the third direction; and then, the mould body M is moved by d2 in the first direction. In a practical application, the mould body may be moved one time or multiple times only in one direction so as to change the location of the mould body, which is not limited in the embodiments of the present disclosure.

After the mould body M is moved to the second coordinate point P2, the X-ray projection of the mould body M on the detection surface Y is a second X-ray projection. In a first implementable manner, the boundary line segment of the second X-ray projection may at least include projection line segments (a line segment Q3 and a line segment Q4, respectively) of the edges of the two first planes in the mould body M on the detection surface Y. In a second implementable manner, the boundary line segment of the second X-ray projection may at least include a projection line segment of an edge of one second plane in the mould body M on the detection surface Y, and the length of the projection line segment is equal to the distance between Q3 and Q4 in FIG. 13.

In step 307, a distance between the focus of the X-ray source and the detection surface, as well as a distance between the focus and the rotation center point is determined according to a geometric relationship among the first X-ray projection, the second X-ray projection, the first coordinate point, and the second coordinate point.

As shown in FIG. 13, after acquiring the first X-ray projection, the second X-ray projection, the first coordinate point, and the second coordinate point, a similar triangle principle in the geometric relationship may be combined (of course, other principles in the geometric relationship may also be combined, which is not limited in the embodiments of the present disclosure) to determine the distance D between the focus S of the X-ray source and the detection surface. For example, if the length of the mould body in the first direction is H and the length of the mould body in the third direction is W, the following three equations can be derived according to the geometric relationship:

$$\frac{H}{\overline{Q1Q2}} = \frac{L_1}{D}; \quad \frac{H+d_2}{\overline{Q1Q4}} = \frac{L_1+d_1}{D}; \text{ and } R = L_1 + \frac{W}{2}.$$

$\overline{Q1Q2}$ represents the distance between the line segment Q1 and the line segment Q2; $\overline{Q1Q4}$ represents the distance between the line segment Q1 and the line segment Q4; and L1 represents the distance from the focus to a surface near the focus in the mould body. By combining the above three equations, the distance D between the focus S and the detection surface, as well as the distance R between the focus and the rotation center point can be obtained. Optionally, R and D are determined by the combining the above three equations in the embodiment of the present disclosure. In a practical application, R and D may be determined by other equations or other manners, which is not limited in the embodiments of the present disclosure.

In a practical application, when the mould body is moved from the first coordinate point to the second coordinate point, Q2 and Q3 may be coincided with each other, which is not limited in the embodiments of the present disclosure.

After the step 307 is executed, the following CT system parameters (a total of five parameters) are obtained in a calibrating manner in the embodiment of the present disclosure: the coordinates of the foot of the perpendicular (including two parameters of a horizontal coordinate and a vertical coordinate in the coordinate system of the foot of the perpendicular on the detection surface) of the focus on the detection surface, the in-plane rotation angle of the detection surface, the distance between the focus and the detection surface, and the distance between the focus and the rotation center point.

Optionally, the mould body used in steps 301 to 307 may be the scanning table in the CT system, or may be the light-limiting door in the CT system. Optionally, the mould body used in step 301 to step 304 and the mould body used in step 305 to step 307 may be different. For example, the mould body used in steps 301 to 304 is the light-limiting door, and the mould body used in steps 305 to 307 is the scanning table, which is not limited in the embodiments of the present disclosure.

In summary, in the method for determining a CT system parameter provided by the embodiment of the present disclosure, the CT system parameter can be determined as long as the used mould body has the first plane and the second plane. Moreover, since the structure of the plane is relatively simple, a manufacturing process of the mould body is relatively simple.

Since the structure of the plane is relatively simple, there is no need to spend more cost in manufacturing the mould body. That is, the cost of manufacturing the mould body used in the embodiments of the present disclosure is lower. Thus, the cost of determining the CT system parameter in the embodiments of the present disclosure is lower.

In addition, since the structure of the mould body used in the related art is relatively complicated (including many small steel balls), the manufactured mould body is apt to have a large error, thereby affecting the accuracy of the determined CT system parameter. In the embodiments of the present disclosure, since the structure of the used mould body is relatively simple (only the first plane and the second plane are required), the error of the manufactured mould body is small and thus the accuracy of the determined CT system parameter is improved.

Optionally, the mould body used in the embodiment of the present disclosure may be the scanning table or the light-limiting door in the CT system. That is, an intrinsic component in the CT system is directly used as the mould body in the embodiment of the present disclosure and thus there is no need to use a customized module body in the process of determining the CT system parameter.

Further, in the process of determining the CT parameter by the method for determining a CT system parameter provided by the embodiment of the present disclosure, only the location of the mould body is required to be adjusted, and both locations of the X-ray source and the detector are not required to be changed, so that the embodiment of the present disclosure can be applicable not only to a CT system in which the X-ray source and the detector are rotatable, but also to a CT system in which the locations of the X-ray source and the detector are unadjustable.

The above embodiments may be implemented in whole or in part by hardware, software, firmware or any one of combinations thereof. When implemented by the software, the embodiments may be implemented in whole or in part in the form of a computer program product including one or more computer instructions. When the computer program instructions are loaded and executed on a computer, processes or functions described in the embodiments of the present disclosure are generated in whole or in part. The computer may be a general-purpose computer, a computer network, or other programmable devices. The computer instructions may be stored in a readable storage medium of the computer or may be transferred from one computer-readable storage medium to another computer-readable storage medium. For example, the computer instructions may be transferred from one website site, computer, server or data center to another website site, computer, server, or data center in a wired (e.g., through a coaxial cable, an optical fiber, or a digital subscriber line) or wireless (e.g., through infrared, wireless, or microwave) manner. The computer-readable storage medium may be any available medium that can be accessed by the computer or data storage equipment such as the server and data center that includes one or more available medium integration. The available medium may be a magnetic medium (e.g., a floppy disk, a hard disk, or a magnetic tape), an optical medium, a semiconductor medium (e.g., a solid-state hard disk), or the like.

It should be noted that in the present disclosure, the embodiments for the method for determining the CT system parameter and the embodiments for the device for determining the CT system parameter can refer to each other, which is not limited in the present disclosure.

The foregoing descriptions are only optional embodiments of the present disclosure, and do not intend to limit the present disclosure. Any variation, equivalent substitution, modification and the like that fall within the spirit and principle of the present disclosure should be embraced by the protective scope of the present disclosure.

In the present disclosure, the terms "first" and "second" are used for descriptive purposes only and should not be construed to indicate or imply the relative importance. The term "a plurality of" refers to two or more, unless explicitly defined otherwise.

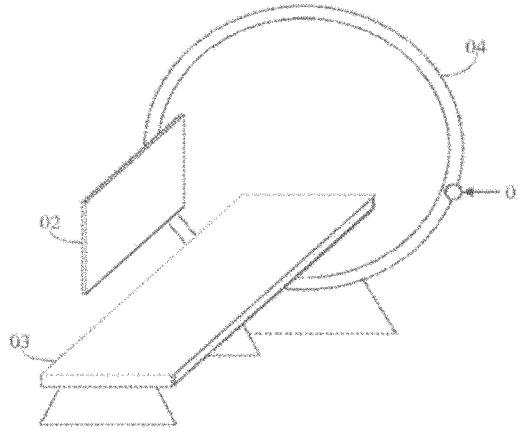

The invention claimed is:

1. A method for determining a computed tomography (CT) system parameter, wherein a CT system comprises an X-ray source and a detector; and the method comprises:
controlling a mould body to move between the X-ray source and a detection surface of the detector and acquiring X-ray projections of the mould body during movement on the detection surface, wherein the mould body has a first plane and a second plane perpendicular to each other, and the first plane and the second plane are always perpendicular to the detection surface during the movement of the mould body;
determining a first straight line and a second straight line according to the acquired X-ray projections, wherein the first straight line is a straight line of a projection line segment of an edge of the first plane in boundary line segments of the acquired X-ray projections, the second straight line is a straight line of a projection line segment of an edge of the second plane in the boundary line segments of the acquired X-ray projections, a plane determined by the first straight line and a focus of the X-ray source is perpendicular to the detection surface, and a plane determined by the second straight line and the focus of the X-ray source is perpendicular to the detection surface; and
determining an intersection point of the first straight line and the second straight line as coordinates of a foot of a perpendicular of the focus of the X-ray source on the detection surface, wherein a CT coordinate system parameter comprises the coordinates of the foot of the perpendicular.

2. The method according to claim 1, wherein the CT system parameter further comprises an in-plane rotation angle of the detector; and the method further comprises:
determining any one of line segments from the boundary line segments of any one of the X-ray projections of the mould body; and
determining the in-plane rotation angle according to the any one of line segments.

3. The method according to claim 1, wherein the CT system parameter further comprises a distance between the focus of the X-ray source and the detection surface; and the method further comprises:
moving the mould body to make a mark point on the mould body to coincide with a first coordinate point, and acquiring a first X-ray projection of the mould body on the detection surface;
controlling the mark point on the mould body to move from the first coordinate point to a second coordinate point, and acquiring a second X-ray projection of the mould body on the detection surface; and
determining the distance between the focus of the X-ray source and the detection surface according to a geometric relationship among the first X-ray projection, the second X-ray projection, the first coordinate point, and the second coordinate point.

4. The method according to claim 3, wherein the CT system parameter further comprises a distance between the focus of the X-ray source and a rotation center point of the CT system and the first coordinate point is located on a plane which passes through the rotation center point and parallel to the first plane, and after acquiring the second X-ray projection of the mould body on the detection surface, the method further comprises:
   determining the distance between the focus of the X-ray source and the rotation center point of the CT system according to the geometric relationship among the first X-ray projection, the second X-ray projection, the first coordinate point, and the second coordinate point.

5. The method according to claim 4, wherein the first coordinate point coincides with the rotation center point.

6. The method according to claim 3, wherein the mark point is located on the first plane.

7. The method according to of claim 1, wherein the mould body has m first planes parallel to each other and m is an integer greater than or equal to 2; and the controlling a mould body to move between the X-ray source and a detection surface of the detector and acquiring the X-ray projections of the mould body during the movement on the detection surface comprise:
   controlling the mould body to move multiple times in a first direction, and acquiring a plurality of third X-ray projections of the mould body on the detection surface, wherein the first direction is perpendicular to the first plane, and boundary line segments of the third X-ray projections comprise projection line segments of edges of two first planes; and
   controlling the mould body to perform at least one periodic movement and acquiring a plurality of fourth X-ray projections of the mould body on the detection surface, until in one periodic movement process of the mould body, projection line segments of edges of the same second plane in boundary line segments of all the fourth X-ray projections of the mould body are located on the same straight line, wherein the periodic movement comprises: moving in a second direction and controlling the mould body to move multiple times in a third direction after the mould body is controlled to move in the second direction, the fourth X-ray projection is the X-ray projection of the mould body on the detection surface during the movement in the third direction, the second direction is perpendicular to the second plane, and the third direction is perpendicular to both the first direction and the second direction; and
   the determining a first straight line and a second straight line according to the acquired X-ray projections comprises:
   screening out a target X-ray projection from the plurality of third X-ray projections, wherein the target X-ray projection is a projection with the minimum distance between the projection line segments of the edges of the two first planes among the boundary line segments of the plurality of third X-ray projections, a reference X-ray projection and the target X-ray projection are two X-ray projections continuously acquired from the plurality of third X-ray projections, a distance between the projection line segments of the edges of the two first planes in the boundary line segments of the target X-ray projection is less than a distance between the projection line segments of the edges of the two first planes in the boundary line segments of the reference X-ray projection;
   determining a straight line of a projection line segment away from a center of the reference X-ray projection in the projection line segments of the edges of the two first planes in the boundary line segment of the target X-ray projection as the first straight line; and
   determining the same straight line as the second straight line.

8. The method according to claim 1, wherein the CT system further comprises a scanning table and a light-limiting door of the X-ray source, and the mould body is the scanning table or the light-limiting door.

9. A device for determining a computed tomography (CT) system parameter comprising:
   at least one processor, at least one interface, a memory and at least one bus; and
   wherein the at least one processor is configured to execute an executable module stored in the memory to implement the method according to claim 1.

10. The device according to claim 9, wherein the at least one processor is a central processing unit.

11. The device according to claim 9, wherein the executable module is a computer program.

12. The device according to claim 9, wherein the at least one interface is configured to implemented the communication connection between the CT system parameter determining device and at least one other device.

13. The device according to claim 9, wherein the memory stores a program that can be executed by the processor.

14. The device according to claim 9, wherein the memory comprises a high-speed random access memory.

15. The device according to claim 14, wherein the memory further comprises a non-volatile memory.

16. The device according to claim 15, wherein the non-volatile memory is at least one magnet disk memory.

17. The device according to claim 9, wherein the memory and the at least one interface are respectively connected to the at least one processor through the at least one bus.

18. The device according to claim 9, wherein the at least one bus is configured to implement connection and communication among the at least one processor, the at least one interface and the memory.

19. A computer-readable storage medium, wherein instructions are stored in the computer-readable storage medium; and when the computer-readable storage medium runs on a computer, the computer is caused to execute the method for determining a CT system parameter according to claim 1.

* * * * *

UNITED STATES PATENT AND TRADEMARK OFFICE
CERTIFICATE OF CORRECTION

PATENT NO. : 10,948,430 B2  
APPLICATION NO. : 16/627255  
DATED : March 16, 2021  
INVENTOR(S) : Hao Yan Page 1 of 2

It is certified that error appears in the above-identified patent and that said Letters Patent is hereby corrected as shown below:

On the Title Page

Column 1, Item (73), Line 2, under Assignee, after "CO., LTD" insert --Shenzhen (CN)--.

Under Abstract, please insert --19 Claims, 8 Drawing Sheets-- as shown on the attached title page.

In the Drawings

Figure 14:
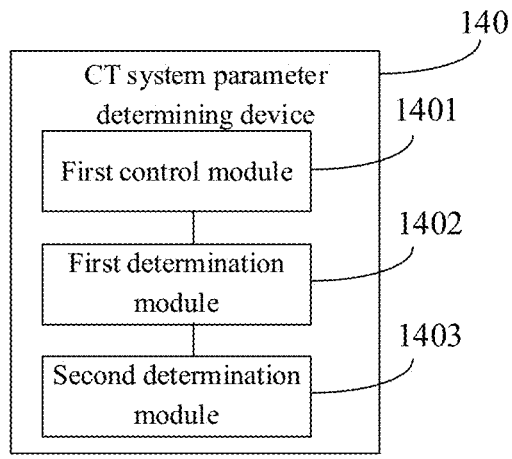

On Sheet 9 of 11, delete FIG. 14.

Figure 15:
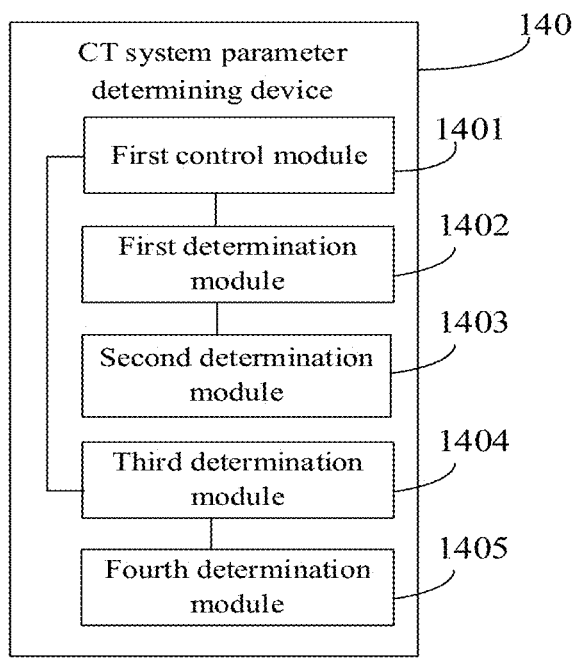

On Sheet 9 of 11, delete FIG. 15.

Figure 16:
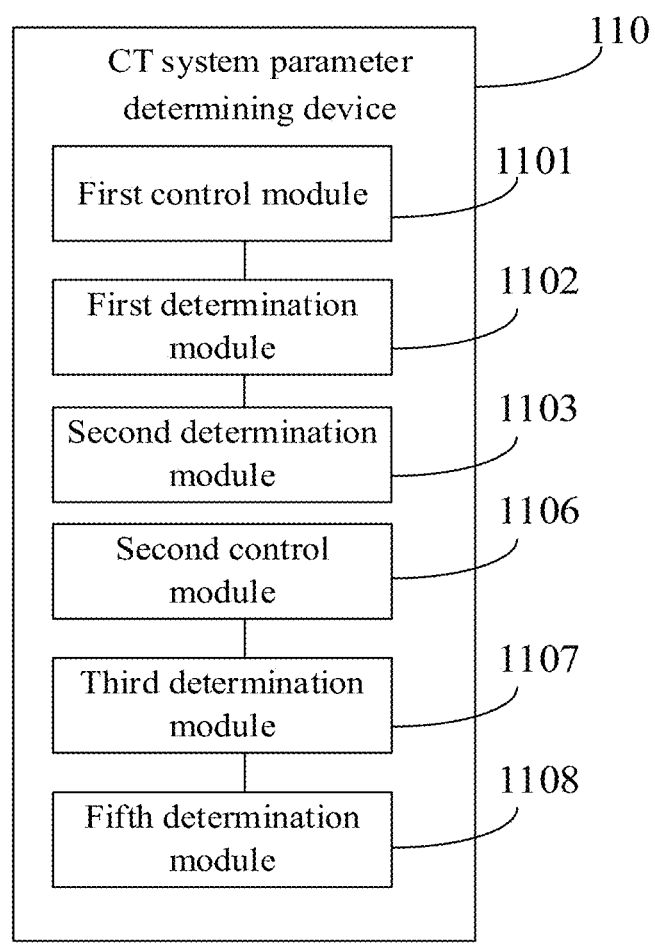

On Sheet 10 of 11, delete FIG. 16.

Figure 17:
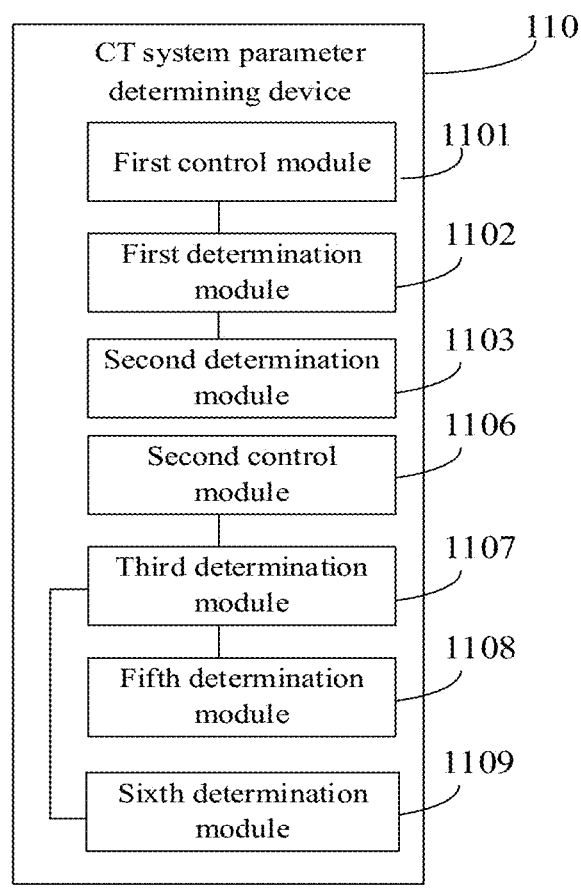

On Sheet 11 of 11, delete FIG. 17.

In the Specification

In Column 8, Line 54, delete "a" and insert --α--.

In the Claims

In Column 13, Line 20, Claim 7, delete "according to of Claim" and insert --according to Claim--.

In Column 14, Line 23, Claim 9, delete "parameter" and insert --parameter,--.

Signed and Sealed this  
Twenty-fourth Day of August, 2021

Drew Hirshfeld  
*Performing the Functions and Duties of the*  
*Under Secretary of Commerce for Intellectual Property and*  
*Director of the United States Patent and Trademark Office*

(12) United States Patent
Yan et al.

(10) Patent No.: US 10,948,430 B2
(45) Date of Patent: Mar. 16, 2021

(54) METHOD AND DEVICE FOR DETERMINING CT SYSTEM PARAMETER

(71) Applicant: Shenzhen Our New Medical Technologies Development Co., Ltd., Shenzhen (CN)

(72) Inventors: Hao Yan, Shenzhen (CN); Wen Wang, Shenzhen (CN); Jinsheng Li, Shenzhen (CN)

(73) Assignee: SHENZHEN OUR NEW MEDICAL TECHNOLOGIES DEV CO., LTD

(*) Notice: Subject to any disclaimer, the term of this patent is extended or adjusted under 35 U.S.C. 154(b) by 0 days.

(21) Appl. No.: 16/627,255

(22) PCT Filed: Jun. 27, 2017

(86) PCT No.: PCT/CN2017/090378
§ 371 (c)(1),
(2) Date: Dec. 27, 2019

(87) PCT Pub. No.: WO2019/000234
PCT Pub. Date: Jan. 3, 2019

(65) Prior Publication Data
US 2020/0132612 A1    Apr. 30, 2020

(51) Int. Cl.
*G01N 23/046*    (2018.01)

(52) U.S. Cl.
CPC ..... *G01N 23/046* (2013.01); *G01N 2223/303* (2013.01); *G01N 2223/306* (2013.01)

(58) Field of Classification Search
CPC ............ G01N 23/046; G01N 2223/303; G01N 2223/306; A61B 6/03; G01B 11/03
See application file for complete search history.

(56) References Cited

U.S. PATENT DOCUMENTS 4,922,915 A * 5/1990 Arnold ................ A61B 6/583 378/18
5,699,446 A * 12/1997 Rougee ................ A61B 6/02 382/130
(Continued)

FOREIGN PATENT DOCUMENTS

| CN | 101750021 A | 6/2010 |
| CN | 102652674 A | 9/2012 |

(Continued)

OTHER PUBLICATIONS

International Search Report in International Patent Application No. PCT/CN2017/090378 dated Mar. 26, 2018, in 4 pages.

*Primary Examiner* — Marcus H Taningco
(74) *Attorney, Agent, or Firm* — Knobbe Martens Olson & Bear LLP

(57) ABSTRACT

A method for determining a CT system parameter: controlling a mould body to move between an X-ray source and a detection surface of a detector, and acquiring X-ray projections of the mould body during movement on the detection surface, wherein the mould body has a first plane and a second plane perpendicular to each other, and the first plane and the second plane are always perpendicular to the detection surface during the movement of the mould body; determining a first straight line and a second straight line according to the acquired X-ray projections; and determining an intersection point of the first straight line and the second straight line as a pedal coordinate of a focus of the X-ray source on the detection surface, a CT coordinate system parameter including the coordinates of the foot of the perpendicular.

19 Claims, 8 Drawing Sheets